United States Patent
Iba et al.

(10) Patent No.: US 10,487,285 B2
(45) Date of Patent: Nov. 26, 2019

(54) METHOD FOR PRODUCING DIALKYL POLYSULFIDE, DIALKYL POLYSULFIDE, EXTREME-PRESSURE ADDITIVE AND LUBRICATING FLUID COMPOSITION

(71) Applicant: DIC Corporation, Tokyo (JP)

(72) Inventors: Takafumi Iba, Ichihara (JP); Hiroshi Sakata, Ichihara (JP)

(73) Assignee: DIC Corporation, Tokyo (JP)

( * ) Notice: Subject to any disclaimer, the term of this patent is extended or adjusted under 35 U.S.C. 154(b) by 570 days.

(21) Appl. No.: 15/023,862

(22) PCT Filed: Sep. 18, 2014

(86) PCT No.: PCT/JP2014/074666
§ 371 (c)(1),
(2) Date: Mar. 22, 2016

(87) PCT Pub. No.: WO2015/046008
PCT Pub. Date: Apr. 2, 2015

(65) Prior Publication Data
US 2016/0215231 A1 Jul. 28, 2016

(30) Foreign Application Priority Data
Sep. 24, 2013 (JP) ................................ 2013-196903

(51) Int. Cl.
*C07C 319/22* (2006.01)
*C10M 135/22* (2006.01)
*C10M 135/04* (2006.01)
*C07C 319/24* (2006.01)
*C07C 321/18* (2006.01)

(52) U.S. Cl.
CPC ......... *C10M 135/22* (2013.01); *C07C 319/22* (2013.01); *C07C 319/24* (2013.01); *C07C 321/18* (2013.01); *C10M 135/04* (2013.01); *C10M 2203/1006* (2013.01); *C10M 2219/022* (2013.01); *C10N 2220/028* (2013.01); *C10N 2230/06* (2013.01); *C10N 2230/12* (2013.01); *C10N 2240/08* (2013.01); *C10N 2240/10* (2013.01); *C10N 2270/00* (2013.01)

(58) Field of Classification Search
CPC .............. C10M 135/22; C10M 135/04; C10M 2219/022; C10M 2203/1006; C07C 319/24; C07C 321/18; C07C 319/22; C10N 2240/10; C10N 2240/08; C10N 2230/12; C10N 2220/028; C10N 2270/00; C10N 2230/06
See application file for complete search history.

(56) References Cited

U.S. PATENT DOCUMENTS

| | | | |
|---|---|---|---|
| 2,614,914 A | 10/1952 | Eby | |
| 2,668,103 A | 2/1954 | Goodhue | |
| 4,125,552 A * | 11/1978 | Speier | C07C 319/24 556/428 |
| 4,191,659 A | 3/1980 | Davis | |
| 4,344,854 A * | 8/1982 | Davis | C07G 17/004 508/324 |
| 4,584,113 A * | 4/1986 | Walsh | C07G 17/006 508/331 |
| 4,937,385 A * | 6/1990 | Buchholz | C07C 319/16 568/21 |
| 5,146,000 A | 9/1992 | Ozbalik | |
| 5,174,922 A | 12/1992 | Perozzi et al. | |
| 5,457,234 A | 10/1995 | Shaw | |

FOREIGN PATENT DOCUMENTS

| | | |
|---|---|---|
| EP | 0554011 A2 | 8/1993 |
| JP | 59-10559 A | 1/1984 |
| JP | 5-125040 A | 5/1993 |
| JP | 2000-239250 A | 9/2000 |
| JP | 2002-193796 A | 7/2002 |
| JP | 2005-146094 A | 6/2005 |

OTHER PUBLICATIONS

Office Action dated Sep. 5, 2016, issued for Chinese patent application No. 201480052839.8. and English translation thereof.
Supplementary European Search Report dated Feb. 24, 2017, issued for the European patent application No. 14849819.9.
Arisawa, Mieko et al., "Oxidation/reduction interconversion of thiols and disulfides using hydrogen and oxygen catalyzed by a rhodium complex," Tetrahedron Letters 46, 2005, pp. 6097-6099.
Mukaiyama, Teruaki et al., "A novel method for the synthesis of thiols from the corresponding olefins by using thiocarbonates and Ti(IV) halides," Chemistry Letters, 2001, pp. 638-639.
Rice, William G. et al., "Evaluation of Selected Chemotypes in Coupled Cellular and Molecular Target-Based Screens Identifies Novel HIV-1 Zinc Finger Inhibitors," Journal of Medicinal Chemistry, 39, 1996, pp. 3606-3616.

(Continued)

Primary Examiner — Taiwo Oladapo
(74) Attorney, Agent, or Firm — Locke Lord LLP

(57) ABSTRACT

For efficiently producing a dialkyl polysulfide which is able to be favorably used as an extreme-pressure additive which does not easily corrode the metal surface, and an extreme-pressure additive and lubricating fluid composition including the dialkyl polysulfide, provided is a method for producing dialkyl polysulfide including a first step of reacting an olefin compound (a) represented by General Formula (1): $R^1R^2C=CHR^3$ (where $R^1$ and $R^2$ each are an alkyl group, $R^3$ is a hydrogen atom or an alkyl group, and the total number of carbon atoms of $R^1$, $R^2$ and $R^3$ is 2 to 20) with sulfur in the presence of a hydrogen sulfide to thereby obtain crude dialkyl polysulfide (A), and a second step of reacting the crude dialkyl polysulfide (A) and a sulfide of an alkali metal in a solvent including an alcohol to thereby reduce the number of sulfur atoms in the crude dialkyl polysulfide (A).

16 Claims, No Drawings

(56) References Cited

OTHER PUBLICATIONS

Sato, Ryu et al., "Novel formations of unsymmetrical 1,2,5-benzotrithiepins from olefins and benzopentathiepin in the presence of Lewis acid. Benzopentathiepin as a novel 1,5-dipole synthon," Chemistry Letters, 12, 1989, pp. 2111-2114.
Kim, Yong Hae et al., "New synthesis of alkyl polysulfides by treatment of thiols, disulfides and thionitrites with anhydrous copper(II) chloride," Bulletin of the Chemical Society of Japan, vol. 52, No. 10, 1979, pp. 3117-3118.
Hartough, H. D., "Color reactions of thiophene derivatives and of other compounds with a ceric nitrate reagent," Analytical Chemistry, 23, 1951, pp. 1128-1130.
International Search Report dated Dec. 22, 2014, issued for PCT/JP2014/074666.

\* cited by examiner

METHOD FOR PRODUCING DIALKYL POLYSULFIDE, DIALKYL POLYSULFIDE, EXTREME-PRESSURE ADDITIVE AND LUBRICATING FLUID COMPOSITION

TECHNICAL FIELD

The present invention relates to a method capable of efficiently producing dialkyl polysulfide, which effectively forms a coating film of metal sulfide on a metal surface and which is able to be favorably used as an extreme-pressure additive which does not easily corrode the metal surface, and also to an extreme-pressure additive including the dialkyl polysulfide and a lubricating fluid composition including the same.

BACKGROUND ART

In the related art, extreme-pressure additives are used for lubricating fluid compositions such as machining oils, plastic working oils, gear oils, sliding surface oils, and grease to prevent friction between metals, reduce wear, and prevent burning. Examples of the extreme-pressure additive include chlorine-containing organic compounds such as chlorinated paraffin and chlorinated fatty acid esters; and sulfur-containing organic compounds such as dialkyl polysulfides including fat sulfides or olefin sulfides, and among these, dialkyl polysulfides are widely used since it is possible to increase the sulfur content of the extreme-pressure additive, and the solubility in the base oil is high, which makes it possible to increase the sulfur content in the base oil.

There is a demand for dialkyl polysulfides used as an extreme-pressure additive to have a performance of forming a coating film of metal sulfide on a metal surface without the metal surface being corroded by the sulfur atoms. Examples of the dialkyl polysulfide include dialkyl monosulfide, dialkyl disulfide, dialkyl trisulfide, dialkyl tetrasulfide, and the like. In general, among the dialkyl sulfides, dialkyl monosulfide and dialkyl disulfide are unable to efficiently form a coating film of a metal sulfide on a metal surface since the number of sulfur atoms in one molecule is small and the reactivity with metal is poor.

Dialkyl trisulfide is known as the ideal dialkyl polysulfide for favorably forming a coating film of metal sulfide on a metal surface without the metal surface being easily corroded by the sulfur atoms. It is known that an olefin, in which two alkyl groups are bonded with a carbon atoms at the second position of 1-olefin, is used as a raw material in order to obtain dialkyl trisulfide. Specifically, a method of reacting diisobutylene and liquid sulfur in the presence of hydrogen sulfide is known (for example, refer to PTL 1).

However, in the method described in PTL 1, the dialkyl polysulfide is obtained as a mixture in which approximately the same amounts of dialkyl trisulfide and dialkyl tetrasulfide are mixed. This dialkyl tetrasulfide reacts excessively well with metal and corrodes the metal surface. Therefore, there is a demand for a method for producing a dialkyl polysulfide which includes, at a high content ratio, the dialkyl trisulfide ideal for favorably forming a coating film of metal sulfide on a metal surface without corroding the metal surface.

CITATION LIST

Patent Literature

[PTL 1] JP-A-2000-239250

SUMMARY OF INVENTION

Technical Problem

The present invention has an object of providing a method for producing a dialkyl polysulfide, which is able to effectively form a coating film of metal sulfide on a metal surface and to be favorably used as an extreme-pressure additive which does not easily corrode the metal surface. In addition, the present invention has an object of providing a dialkyl polysulfide, which is able to effectively form a coating film of metal sulfide on a metal surface and to be favorably used as an extreme-pressure additive which does not easily corrode the metal surface; an extreme-pressure additive including this dialkyl polysulfide; and a lubricating fluid containing the same.

Solution to Problem

As the result of extensive studies to solve the problems described above, the present inventors have found out that, after obtaining a crude dialkyl polysulfide by reacting an olefin in which two alkyl groups are bonded with a carbon atom at the second position in 1-olefin with sulfur in the presence of hydrogen sulfide, by reacting the obtained crude dialkyl polysulfide with a sulfide of an alkali metal in a solvent including an alcohol, a mixture of dialkyl polysulfide which includes ideal dialkyl trisulfide at high efficiency as an extreme-pressure additive can be obtained. The present inventors also have found out that, with respect to a mixture of dialkyl polysulfides each having an alkyl group having a specific structure, a dialkyl polysulfide in which the content ratio of the dialkyl disulfide and the dialkyl trisulfide is in a specific range is able to effectively form a coating film of metal sulfide on a metal surface, does not easily corrode the metal surface, and is able to be favorably used as an extreme-pressure additive, thereby completing the present invention.

That is, the present invention provides a method for producing dialkyl polysulfide, the method including a first step of reacting an olefin compound (a) represented by General Formula (1):

$$R^1R^2C=CHR^3 \tag{1}$$

(where $R^1$ and $R^2$ each are an alkyl group, $R^3$ is a hydrogen atom or an alkyl group, and the total number of carbon atoms of $R^1$, $R^2$ and $R^3$ is 2 to 20)
with sulfur in the presence of hydrogen sulfide to thereby obtain a crude dialkyl polysulfide (A), and
a second step of reacting the crude dialkyl polysulfide (A) with the sulfide of an alkali metal in a solvent which includes an alcohol to thereby reduce the number of sulfur atoms in the crude dialkyl polysulfide (A).

In addition, the present invention provides a dialkyl polysulfide represented by General Formula (2) below:

[Chem. 1]

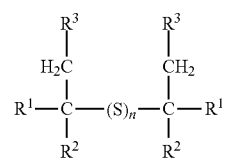

(2)

(where $R^1$ and $R^2$ each are an alkyl group, $R^3$ is a hydrogen atom or an alkyl group, the total number of carbon atoms in one of $R^1$, one of $R^2$, and one of $R^3$ is 2 to 20, and n is an integer of 1 to 6), the sum of the content ratio of the compound of General Formula (2) in which n is 2 and the content ratio of the compound of General Formula (2) in which n is 3 being 80 mass % to 100 mass % with respect to the total amount of the compound represented by General Formula (2).

In addition, the present invention provides an extreme-pressure additive which contains the dialkyl polysulfide (I).

Furthermore, the present invention provides a lubricating fluid composition which contains the extreme-pressure additive.

Advantageous Effects of Invention

Using the production method of the present invention, it is possible to efficiently obtain a dialkyl polysulfide which is able to effectively form a coating film of metal sulfide on a metal surface, which does not easily corrode the metal surface, and which is able to be favorably used as an extreme-pressure additive. In addition, the dialkyl polysulfide of the present invention is able to effectively form a coating film of metal sulfide on a metal surface, does not easily corrode the metal surface, and is able to be favorably used as an extreme-pressure additive.

DESCRIPTION OF EMBODIMENTS

The production method of the present invention includes the following steps.

First step: a step of reacting an olefin compound (a) which is represented by General Formula (1) below:

(where $R^1$ and $R^2$ each are an alkyl group, $R^3$ is a hydrogen atom or an alkyl group, and the total number of carbon atoms of R', $R^2$ and $R^3$ is 2 to 20) with sulfur in the presence of a hydrogen sulfide to thereby obtain a crude dialkyl polysulfide (A)

Second step: a step of reacting the crude dialkyl polysulfide (A) with a sulfide of an alkali metal in a solvent including an alcohol to thereby reduce a number of sulfur atoms in the crude dialkyl polysulfide (A)

Detailed description of each of the steps will be given below.

The olefin compound (a) used in the first step has a structure represented by General Formula (1) as described above. Among the olefin compounds (a), an olefin compound of General Formula (1) in which the total number of carbon atoms of $R^1$ and $R^2$ is 2 to 18 is preferable since it is easily available and the dialkyl polysulfide, which is the final product, has favorable solubility in a base oil and can be preferably used as an extreme-pressure additive, and an olefin compound of General Formula (1) in which the total number of carbon atoms of $R^1$ and $R^2$ is 2 to 14 is more preferable.

In addition, among the olefin compounds (a), an olefin compound which has a hydrogen atom as $R^3$ is preferable since it is easily available and the dialkyl polysulfide, which is the final product, has favorable solubility in a base oil and can be preferably used as an extreme-pressure additive.

Accordingly, among the olefin compounds (a) which have a structure represented by General Formula (1), an olefin compound of General Formula (1) in which the total number of carbon atoms of $R^1$ and $R^2$ is 2 to 18 and $R^3$ is a hydrogen atom is preferable, and an olefin compound of General Formula (1) in which the total number of carbon atoms of $R^1$ and $R^2$ is 2 to 14 and $R^3$ is a hydrogen atom is more preferable.

Examples of the olefin compound (a) which is used in the present invention include diisobutylene, isobutylene, 3-methylpentene, 4-methylheptene, 5-methylundecene, 3,6-dimethylhexanedecene, and the like. Among these, diisobutylene is preferable since a dialkyl polysulfide with a high sulfur content ratio and less odor can be obtained.

Here, in the production method of the present invention, it is also possible to use an olefin compound other than the olefin compound (a) in combination with the olefin compound (a) in a range which does not impair the effects of the present invention. Examples of such olefin compounds include 1-butene, 1-pentene, 1-hexene, 1-octene, 1-decene, 1-dodecene, 1-tetradecene, 1-hexadecene, 1-octadecene, 1-eicosene, mixtures thereof, and the like.

The sulfur which is used in the present invention is not particularly limited and, for example, the sulfur may be in a solid state of small lumps, flakes, or a powder, or may be in a molten state (a liquid). Among these, sulfur in the molten state is preferable since the preparation work is easy in large-scale production.

The hydrogen sulfide (a3) is also not particularly limited; however, it is preferable to use the hydrogen sulfide (a3) having a purity of 99 mol % or higher from the point of view of obtaining the dialkyl polysulfide of the present invention with high purity.

In the first step, when reacting the olefin compound (a) with sulfur in the presence of hydrogen sulfide, the reaction is preferably carried out in the presence of a basic compound (catalyst) since it is possible to efficiently and easily obtain the crude dialkyl polysulfide (A). Examples of the basic compounds may include alkali metal hydroxides such as sodium hydroxide and potassium hydroxide, or amine-based compounds such as aliphatic amines and aromatic amines. Examples of the amine-based compounds include butylamine, dibutylamine, tributylamine, various kinds of isomers thereof, octyl amine, dioctyl amine, various kinds of isomers thereof, dodecylamine, tetradecylamine, hexadecylamine, octadecylamine, dicyclohexylamine, various kinds of isomers thereof, methylene diamine, ethylene diamine, 1,2-diaminopropane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, and the like, diethylenetriamine, dipropylenetriamine, triethylenetetramine, tripropylene tetramine, tetraethylene pentamine, tetrapropylene pentamine, pentaethylene hexamine, nonaethylene decaamine, trimethyl hexamethylene diamine, and the like, tetra(aminomethyl) methane, tetrakis (2-aminoethyl aminomethyl) methane, 1,3-bis (2'-aminoethylamino) propane, triethylene-bis (trimethylene) hexamine, bis (3-aminoethyl) amine, bis hexamethylene triamine, and the like, 1,4-cyclohexane diamine, 4,4'-methylene bis cyclohexylamine, 4,4'-isopropylidene bis cyclohexylamine, norbornadiamine, bis (aminomethyl) cyclohexane, diaminodicyclohexylmethane, isophoronediamine, menthenediamine, and the like, bis (aminoalkyl) benzene, bis (aminoalkyl) naphthalene, bis (cyanoethyl) diethylenetriamine, o-xylylene diamine, m-xylylene diamine, p-xylylene diamine, phenylene diamine, naphthylene diamine, diaminodiphenyl methane, diaminodiethylphenyl methane, 2,2-bis (4-aminophenyl) propane, 4,4'-diaminophenyl ether, 4,4'-diaminobenzophenone, 4,4'-diaminodiphenyl ether, 4,4'-diaminodiphenyl sulfone, 2,2'-dimethyl-4,4'-diaminodiphenylmethane, 2,4'-diamino biphenyl, 2,3'-dimethyl-4,4'-diamino biphenyl, 3,3'-dimethoxy-4,4'-diaminobiphenyl, bis (aminomethyl) naphthalene, bis (aminoethyl) naphthalene, and the like, N-methylpiperazine, morpholine, 1,4-bis-(8-aminopropyl)-piperazine, piperazine-1,4-diazacyclo heptane, 1-(2'-amino ethyl piperazine), 1-[2'-(2"-aminoethylamino)ethyl] piperazine, 1,11-diazacyclo eicosane, 1,15-diazacyclooctacosane, and the like, and these examples may be used individually or as a mixture of two or more types thereof.

Among the basic compounds, alkali metal hydroxides are preferable since it is possible to obtain crude dialkyl polysulfide (A) with high yield and to carry out separation and removal from the reaction system by a simple method such as distillation or ventilation after the reaction, and among these, sodium hydroxide or potassium hydroxide are more preferable, and potassium hydroxide is even more preferable.

The amount of the basic compound to be used is appropriately selected depending on the desired reaction speed; however, it is preferably used in a small amount as long as the reactivity is not deteriorated. It is preferably 0.05 mass % to 1.0 mass %, more preferably 0.1 mass % to 0.5 mass % with respect to the total mass of the olefin compound (a) and sulfur.

In the first step, it is also possible to react the olefin compound (a) with the sulfur in the presence of a basic solvent. Carrying out the reaction in the presence of a basic solvent makes it possible to improve the reaction efficiency of the olefin compound (a) and sulfur. Examples of the basic solvent include cyclic amides, straight-chain amides, amines, and the like.

Examples of the cyclic amides include N-methyl pyrrolidone, N-ethyl pyrrolidone, N,N-dimethyl propylene urea, 1,3-dimethyl-2-imidazolidinone, and the like. Examples of the straight-chain amides include N,N-dimethylformamide, dimethylacetamide, diethylformamide, tetramethylurea, and the like. Examples of the amines include triethylamine, pyridine, tributylamine, and the like.

Here, in the case of using a basic solvent in the first step, it is possible to expect a certain degree of improvement in the reaction efficiency without adding the basic compound (catalyst) to the reaction system; however, it is preferable to add the basic compound (catalyst) to the reaction system in order to further improve the reaction efficiency even in the case of using a basic solvent.

In the first step, the ratio of the olefin compound (a) and sulfur to be used is preferably 0.5 to 2 mol of sulfur per mol of the olefin (a) since it is possible to lower the content ratio of polysulfides which are tetrasulfides or higher polysulfides in the crude dialkyl polysulfide (A), and more preferably 0.7 to 1.8 mol.

In addition, in the first step, the ratio of the olefin compound (a) and hydrogen sulfide to be used is preferably 0.3 to 0.8 mol of hydrogen sulfide per mol of olefin (a) since it is possible to reduce the unreacted olefin content in the reaction system in the first step, and more preferably 0.4 to 0.7 mol.

In the first step, the reaction temperature when reacting the olefin compound (a) with the sulfur in the presence of hydrogen sulfide is, for example, 50° C. to 150° C., and preferably 60° C. to 130° C. In addition, the time for the reaction is preferably 1 to 72 hours, and more preferably 5 to 48 hours.

The second step is a step of reacting the crude dialkyl polysulfide (A) which was obtained in the first step with a sulfide of an alkali metal in a solvent including an alcohol to thereby reduce the number of sulfur atoms in the crude dialkyl polysulfide (A). Carrying out the reaction in a solvent including an alcohol makes it possible to improve the reactivity between the crude dialkyl polysulfide (A) and the sulfide of an alkali metal and to more efficiently obtain a dialkyl polysulfide which includes dialkyl trisulfide at a high content ratio.

Examples of the sulfides of the alkali metals include sodium sulfide, potassium sulfide, sodium polysulfide, sodium hydrosulfide, potassium hydrosulfide, and the like. Among these, sodium sulfide is preferable since sodium sulfide has a strong effect of reducing the number of sulfur atoms from the sulfur chain in the crude dialkyl polysulfide (A), thereby efficiently obtaining a dialkyl polysulfide (a mixture) including a large amount of dialkyl trisulfide, which is the finally objective material of the present invention.

In the second step, the amount of the sulfide of the alkali metal to be used is preferably 5 to 50 parts by mass, more preferably 10 to 45 parts by mass with respect to 100 parts by mass of the crude dialkyl polysulfide (A) from the viewpoint of the strong effect of reducing the number of sulfur atoms from the sulfur chain in the crude dialkyl polysulfide (A).

Examples of the alcohols include monoalcohols such as methanol, ethanol, n-propanol, iso-propanol, n-butanol, iso-butanol, sec-butanol, tert-butanol, n-pentanol, iso-pentanol, 2-methyl butanol, sec-pentanol, tert-pentanol, 3-methoxy butanol, n-hexanol, 2-methyl pentanol, sec-hexanol, 2-ethyl butanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethyl nonyl alcohol, sec-tetradecyl alcohol, sec-heptadecyl alcohol, furfuryl alcohol, phenol, cyclohexanol, methyl cyclohexanol, 3,3,5-trimethyl cyclohexanol, benzyl alcohol, and diacetone alcohol;

polyhydric alcohols such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, and tripropylene glycol;

polyhydric alcohol partial ethers such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, and dipropylene glycol monopropyl ether; and the like. These alcohols may be used individually or two or more types thereof may be used together.

The content of the alcohol in the solvent including the alcohol is preferably 45 to 75 parts by mass with respect to 100 parts by mass of the solvent, and more preferably 50 to 60 parts by mass, since the sulfide of an alkali metal is easily dissolved and that the reactivity of the crude dialkyl polysulfide (A) with the sulfide is also favorable.

Among the alcohols, preferable are polyhydric alcohols, among which ethylene glycol is more preferable, since the reaction of the crude dialkyl polysulfide (A) with the sulfide of an alkali metal proceeds rapidly and it is possible to efficiently obtain a dialkyl polysulfide (a mixture) which includes a large amount of dialkyl trisulfide which is the ultimate object of the present invention.

It is possible for the solvent including the alcohol to contain a solvent other than an alcohol in a range which does not impair the effects of the present invention. Examples of solvents other than an alcohol include water, ketone-based solvents, cyclic amides, straight-chain amides, and the like.

Examples of the ketone-based solvents include acetone, and the like. Examples of the cyclic amides include N-methyl pyrrolidone, N-ethyl pyrrolidone, N,N-dimethyl propylene urea, 1,3-dimethyl-2-imidazolidinone, and the like. Examples of the straight-chain amides include N,N-dimethylformamide, dimethylacetamide, diethylformamide, tetramethylurea, and the like.

In addition, it is also possible to use a polar solvent such as dimethyl sulfoxide in a range which does not impair the effects of the present invention.

The amount of the solvent to be used is preferably 50 mass % to 300 mass % with respect to the mass of the sulfide of the alkali metal, and more preferably 80 mass % to 250 mass %.

In the first step, in the case of obtaining the crude dialkyl polysulfide (A) by reacting the olefin compound (a) with the sulfur in the presence of hydrogen sulfide and in the presence of a solvent, it is possible for the reaction to proceed in the solvent including the alcohol in the second step, after the crude dialkyl polysulfide (A) is recovered by various methods such as, for example, distillation or washing with water.

The temperature of the reaction system in the second step is preferably 40° C. to 120° C., and more preferably 50° C. to 100° C. since it is possible to efficiently increase the content of dialkyl trisulfide in the final product (dialkyl polysulfide) and side reactions such as decomposition are suppressed. In addition, the time for the reaction is usually 1 to 36 hours, and more preferably 5 to 24 hours.

In the second step, mercaptans which are produced as by-product in the first step are extracted with the alcohol layer since alkali metal hydroxide is included in the reaction system, and hence, a dialkyl polysulfide with less odor can be obtained as a final product. Examples of the alkali metal hydroxides include sodium hydroxide, potassium hydroxide, lithium hydroxide, rubidium hydroxide, cesium hydroxide, and the like. Among these, sodium hydroxide and potassium hydroxide are preferable since they have high solubility in alcohol-based solvents.

The amount of the alkali metal hydroxide to be used is preferably 0.5 to 20 parts by mass with respect to 100 parts by mass of the crude dialkyl polysulfides (A) and more preferably 1 to 10 parts by mass since it is possible to maintain the solubility in a solvent including an alcohol.

After completion of the second step, it is also possible to use the reaction liquid as it is as an extreme-pressure additive; however, the dialkyl polysulfide which is the final product may be obtained by using a conventional method for separating the liquid, followed by filtering the solids or distilling, or separating volatile content.

The dialkyl polysulfide which is obtained by the production method of the present invention is a mixture of dialkyl polysulfides with different numbers of sulfur atoms. The content ratio of each of the dialkyl polysulfides with different numbers of sulfur atoms is determined according to the peak area of a chart obtained by high performance liquid chromatography (hereinafter abbreviated as "HPLC") measurement. Here, the HPLC measurement conditions are as follows.

[HPLC Measurement Conditions]
Measuring apparatus: LC-10A manufactured by Shimadzu Corporation
Column: INTERSIL-C8 4.5 μm 250 mm×4.6 mm
Detector: UV210 nm
Eluent: acetonitrile/water (volume ratio)=85/15, flow rate 1 ml/min The amount of active sulfur in the dialkyl polysulfide which is obtained by the production method of the present invention is preferably 0.1 mass % to 30 mass % based on the total sulfur content and more preferably 0.5 mass % to 20 mass % based on the total sulfur content, since the dialkyl polysulfide effectively forms a coating film of a metal sulfide on a metal surface and does not easily corrode the metal surface. Here, the amount of active sulfur in the present invention is a value which is determined by the method set out in ASTM-D1662.

In addition, the 50% thermal decomposition temperature of the dialkyl polysulfide which is obtained by the production method of the present invention is, for example, 200° C. to 300° C. The thermal decomposition temperature increases as the chain length of the alkyl group of the dialkyl polysulfide which is obtained by the production method of the present invention increases. Accordingly, it is possible to obtain a dialkyl polysulfide (a mixture) having the desired thermal decomposition temperature by mixing dialkyl polysulfides having alkyl groups with different chain lengths.

The dialkyl polysulfide of the present invention is represented by General Formula (2) below.

[Chem. 2]

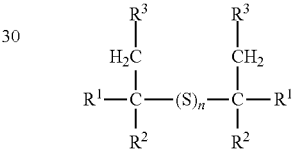

(2)

In the formula, $R^1$ and $R^2$ each are an alkyl group, $R^3$ is a hydrogen atom or an alkyl group, the total number of carbon atoms of one of $R^1$, one of $R^2$ and one of $R^3$ is 2 to 20, and n is an integer of 1 to 6), in which the sum of the content ratio of the compound of General Formula (2) in which n is 2 and the content ratio of the compound of General Formula (2) in which n is 3 is 80 mass % to 100 mass % with respect to the total amount of the compound which is represented by General Formula (2).

Since the sum of the content ratio of the compound in which n is 2 and the content ratio of the compound in which n is 3 is set in this range, the dialkyl polysulfide effectively forms a coating film of metal sulfide on a metal surface, does not easily corrode the metal surface, and is able to be favorably used as an extreme-pressure additive. The content ratio is preferably 85 mass % to 100 mass %, more preferably 85 mass % to 95 mass %, and even more preferably 90 mass % to 95 mass % since the metal surface is corroded less easily and the coating film of metal sulfide is effectively formed on the metal surface.

In General Formula (2), a dialkyl polysulfide in which the total number of carbon atoms of $R^1$ and $R^2$ is 2 to 18 is preferable since the dialkyl polysulfide can be preferably used as an extreme-pressure additive because of the favorable solubility in a base oil, and a dialkyl polysulfide in which the total number of carbon atoms of $R^1$ and $R^2$ is 2 to 14 is more preferable.

In addition, with respect to General Formula (2), a dialkyl polysulfide in which $R^3$ is a hydrogen atom is preferable since the dialkyl polysulfide can be preferably used as an extreme-pressure additive because of the favorable solubility in a base oil.

Accordingly, among the dialkyl polysulfides having the structure represented by General Formula (2), a dialkyl polysulfide in which the total number of carbon atoms of $R^1$ and $R^2$ is 2 to 18 and $R^3$ is a hydrogen atom is preferable, and a dialkyl polysulfide in which the total number of carbon atoms of $R^1$ and $R^2$ is 2 to 14 and $R^3$ is a hydrogen atom is more preferable.

The dialkyl polysulfide of the present invention is easily obtained by, for example, the method for producing dialkyl polysulfide of the present invention.

The extreme-pressure additive of the present invention contains the dialkyl polysulfide (in the present invention, this may be abbreviated as the "dialkyl polysulfide (I)") of the present invention described above. The extreme-pressure additive of the present invention may be formed of only the dialkyl polysulfide (I), or may include dialkyl polysulfides other than the dialkyl polysulfide (I). Preferable examples of the dialkyl polysulfide include a dialkyl polysulfide which is represented by, for example, General Formula (3) below.

[Chem. 3]

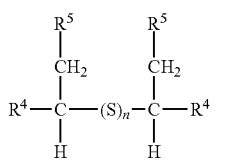

(3)

In the formula, $R^4$ and $R^5$ each are a hydrogen atom or an alkyl group, the total number of carbon atoms of one of $R^4$ and one of $R^5$ is 4 to 20, and n is an integer of 1 to 6), in which the total of the content ratio of the compound in which n in General Formula (3) is 2 and the content ratio of the compound in which n in General Formula (3) is 3 is 80 mass % to 100 mass % with respect to the total amount of the compound which is represented by General Formula (3) (in the present invention, this may be abbreviated as "dialkyl polysulfide (II)"). Detailed description of the dialkyl polysulfide (II) will be given below.

Among the dialkyl polysulfides (II), a dialkyl polysulfide in which the sum of the content ratio of the compound in which n in General Formula (3) is 2 and the content ratio of the compound in which n in General Formula (3) is 3 is 80 mass % to 100 mass % with respect to the total amount of the compound which is represented by General Formula (3) is preferable, the total of the content ratios being more preferably 85 mass % to 95 mass %, and being even more preferably 90 mass % to 95 mass %, since the metal surface is not easily corroded, a coating film of metal sulfide is effectively formed on the metal surface even with the addition of a small amount of the dialkyl polysulfide, and the dialkyl polysulfide is easily obtained.

In General Formula (3), examples of $R^4$ and $R^5$ include a straight-chain alkyl group, a branched alkyl group, and the like. Examples of the straight-chain alkyl group include a methyl group, an ethyl group, a n-butyl group, a n-pentyl group, a n-octyl group, a n-decyl group, a n-dodecyl group, a n-hexadecyl group, a n-octadecyl group, and the like. In addition, examples of the branched alkyl group include a 3-methylpentyl group, a 4-methylheptyl group, a 5-methylundecyl group, a 3,6-dimethyl hexane decyl group, and the like.

Among the dialkyl polysulfides (II), a dialkyl polysulfide in which the total number of carbon atoms of one of $R^4$ and one of $R^5$ is 4 to 16 is preferable, and a dialkyl polysulfide in which the total number of carbon atoms of one of $R^4$ and one of $R^5$ is 4 to 10 is more preferable, since it is possible to maintain a high sulfur content, it is possible to favorably form a metal sulfide film on the metal surface, and the amount of low molecular weight mercaptans which cause an odor decreases.

The amount of active sulfur in the dialkyl polysulfide (II) is preferably 0.1 mass % to 30 mass % based on the total sulfur amount, and more preferably 0.5 mass % to 20 mass % based on the total sulfur amount, since the dialkyl polysulfide effectively forms a coating film of a metal sulfide on a metal surface and does not easily corrode the metal surface. Here, the amount of active sulfur in the present invention is a value which is determined by the method set out in ASTM-D1662.

In addition, the 50% thermal decomposition temperature of the dialkyl polysulfide (II) is, for example, from 200° C. to 300° C. The thermal decomposition temperature increases as the chain length of the alkyl groups of $R^4$ and $R^5$ in General Formula (2) increases. Accordingly, it is possible to obtain a dialkyl polysulfide (a mixture) having the desired thermal decomposition temperature by mixing dialkyl polysulfides having alkyl groups with different chain lengths.

The dialkyl polysulfide (II) is favorably obtained, for example, by using the production method of the present invention which includes the following steps.

Step 1: a step of obtaining a crude dialkyl polysulfide (B) by reacting an olefin compound (b) which is represented by General Formula (4) below:

$$R^4HC=CHR^5 \qquad (4)$$

(in the formula, $R^4$ and $R^5$ each are a hydrogen atom or an alkyl group, and the total number of carbon atoms of $R^4$ and $R^5$ is 4 to 20) with sulfur in the presence of hydrogen sulfide.

Step 2: a step of by reacting the crude dialkyl polysulfide (B) with a sulfide of an alkali metal to thereby reduce the number of sulfur atoms in the crude dialkyl polysulfide (B).

Detailed description of each step will be given below.

The olefin compound (b) which is used in step 1 has a structure represented by General Formula (4) as described above. Among the dialkyl polysulfides (II), a dialkyl polysulfide which is obtained by using, as the olefin compound (b), an olefin compound in which the total number of carbon atoms of $R^4$ and $R^5$ is 4 to 16 is preferable since it is possible to maintain a high sulfur content, it is possible to favorably form a metal sulfide film on a metal surface, and the content of low molecular weight mercaptans which cause an odor decreases, and a dialkyl polysulfide which is obtained by using an olefin compound in which the total number of carbon atoms of $R^4$ and $R^5$ is 4 to 10 is more preferable. Further, a dialkyl polysulfide which is obtained by using, as the olefin compound (b), an olefin compound in which $R^4$ is an alkyl group with 4 to 16 carbon atoms and $R^5$ is a hydrogen atom is preferable since the reactivity is excellent and it is possible to efficiently obtain the dialkyl polysulfide (II), and a dialkyl polysulfide which is obtained by using an olefin compound in which $R^4$ is an alkyl group with 4 to 10 carbon atoms and $R^5$ is a hydrogen atom is more preferable.

Examples of the olefin compounds (b) include a straight-chain 1-olefin and a branched 1-olefin having a branched structure other than the terminal. Examples of the straight-chain 1-olefins include 1-butene, 1-pentene, 1-hexene, 1-octene, 1-decene, 1-dodecene, 1-tetradecene, 1-hexadecene, 1-octadecene, 1-eicosene, mixtures thereof, or the like.

Among the olefin compounds (b), a straight-chain 1-olefin is preferable since it is easily available in industry and the reaction with sulfur proceeds smoothly. Among the straight-chain 1-olefins, an olefin compound with 6 to 18 carbon atoms is preferable, and, among these, an olefin compound with 6 to 12 carbon atoms is more preferable since the pour point is low and it is possible to maintain a liquid state at room temperature.

As the sulfur, for example, it is possible to use the sulfur which can be used in the production method of the present invention. Among these, sulfur in a molten state is preferable since the preparation work is easy in large-scale production.

The hydrogen sulfide is also not particularly limited; however, it is preferable to use hydrogen sulfide having a purity of 99 mol % or more from the point of view of obtaining a dialkyl polysulfide having a high purity among the dialkyl polysulfides (II).

In step 1, for efficiently obtain a dialkyl polysulfide (II), when reacting an olefin compound (b) with sulfur in the presence of hydrogen sulfide in obtaining a crude dialkyl polysulfide (B), it is preferable to carry out the reaction in the presence of a basic compound (catalyst). As the basic catalyst, for example, it is possible to use the basic compounds which can be used in the first step of the production method of the present invention. Among the basic compounds, alkali metal hydroxides are preferable, and sodium hydroxide or potassium hydroxide is more preferable, among those, and potassium hydroxide is even more preferable, since the yield of a crude dialkyl polysulfide (B) is high and separation and removal of the basic compound from the reaction system can be performed by a simple method such as distillation and ventilation after the reaction, thereby efficiently obtaining dialkyl polysulfide (II).

The amount of the basic compound to be used is appropriately selected depending on the reaction speed as desired; however, it is preferably a smaller amount as long as the reactivity is not deteriorated. It is preferably 0.05 mass % to 1.0 mass %, more preferably 0.1 mass % to 0.5 mass % with respect to the total mass of the olefin compound (b) and sulfur.

It is also possible to carry out step 1 in the presence of a basic solvent, since it is possible to shorten the sulfur chain in the crude dialkyl polysulfide (B) to be obtained and efficiently produce the dialkyl polysulfide (II). Examples of the basic solvent include cyclic amides, straight-chain amides, amines, and the like.

Examples of the cyclic amides include N-methyl pyrrolidone, N-ethyl-pyrrolidone, N,N-dimethyl propylene urea, 1,3-dimethyl-2-imidazolidinone, and the like. Examples of the straight-chain amides include N,N-dimethylformamide, dimethylacetamide, diethylformamide, tetramethylurea, and the like. Examples of the amines include triethylamine, pyridine, tributylamine, and the like.

Among the basic solvents, cyclic amides are preferable, and N-methyl pyrrolidone is more preferable among these.

Here, in step 1, it is possible to expect a certain degree of improvement in the reaction efficiency without adding the basic compound (catalyst) to the reaction system in the case of using a basic solvent; however, it is preferable to add the basic compound (catalyst) to the reaction system even in the case of using a basic solvent in order to further improve the reaction efficiency.

In the case of using the basic solvent in step 1, the amount of the basic solvent to be used is preferably 0.5 mass % to 10 mass %, more preferably 1 mass % to 5 mass %, with respect to the olefin compound (b).

In step 1, the ratio of the olefin compound (b) and sulfur to be used is preferably 0.5 to 2 mol of sulfur per mol of the olefin (b) since it is possible to lower the content ratio of polysulfides, which are tetrasulfide or higher polysulfide, in the crude dialkyl polysulfides (B), and is more preferably 0.7 to 1.8 mol of sulfur per mol of the olefin (b).

In addition, in step 1, the ratio of olefin compound (b) and hydrogen sulfide to be used is preferably 0.3 to 0.8 mol, more preferably 0.4 to 0.7 mol of hydrogen sulfide per mol of olefin (b) since it is possible to reduce the unreacted olefin content in the reaction system in step 1.

In step 1, the reaction temperature when reacting an olefin compound (b) with sulfur in the presence of hydrogen sulfide is, for example, 50° C. to 150° C., and preferably 60° C. to 130° C.

In step 1, it is possible to obtain the crude dialkyl polysulfide (B) by reacting the olefin compound (b) with sulfur in the presence of hydrogen sulfide. The crude dialkyl polysulfide (B) is a mixture of those having various sulfur chain lengths and includes dialkyl monosulfides which have poor reactivity, and with which it is difficult to favorably form a film of a metal sulfide on a metal surface. After reacting the olefin compound (b) with sulfur in the presence of hydrogen sulfide, it is possible to efficiently convert the dialkyl monosulfides into a dialkyl polysulfide which has excellent reactivity and favorably and easily forms a film of a metal sulfide on a metal surface by further maintaining the reaction system at a high temperature. Here, the temperature at which the reaction system is maintained is preferably 150° C. to 250° C., and more preferably 160° C. to 200° C. The maintenance time is preferably 1 to 72 hours, and more preferably 5 to 48 hours.

Step 2 is a step of reducing the number of sulfur atoms in the crude dialkyl polysulfide (B) by reacting the crude dialkyl polysulfide (B) which was obtained in step 1 with a sulfide of an alkali metal. Through this step, it is possible to efficiently obtain the dialkyl polysulfide (II) by reducing the sulfur atoms of the sulfur chain in the crude dialkyl polysulfide (B).

Examples of the sulfides of the alkali metals include sodium sulfide, potassium sulfide, sodium polysulfide, sodium hydrosulfide, potassium hydrosulfide, and the like. Among these, sodium sulfide is preferable since the effect of reducing sulfur atoms from the sulfur chain in the crude dialkyl polysulfide (B) is strong and it is possible to efficiently obtain the dialkyl polysulfide (II).

In step 2, the amount of the sulfide of the alkali metal to be used is preferably 5 to 50 parts by mass with respect to 100 parts by mass of the crude dialkyl polysulfide (B), and more preferably 10 to 45 parts by mass, from the point of view of the strong effect of reducing the number of sulfur atoms from the sulfur chain in the crude dialkyl polysulfide (B).

In step 2, the crude dialkyl polysulfide (B) is usually reacted with the sulfide of an alkali metal in a reaction solvent. Examples of the reaction solvent include water, alcohols, cyclic amides, straight-chain amides, and the like, and it is possible to use the solvents which are able to be used in the second step of the production method of the present invention above. Among these, a solvent including an alcohol is preferable since it is possible to efficiently obtain the dialkyl polysulfide (II) because the reaction of the crude dialkyl polysulfide (B) with the sulfide of an alkali metal proceeds rapidly. Among the alcohols, polyhydric alcohols are preferable, and ethylene glycol is more preferable.

The amount of the solvent to be used is preferably 50 mass % to 300 mass % with respect to the mass of the sulfide of the alkali metal, and more preferably 80 mass % to 250 mass %.

Here, in step 1, in the case of obtaining the crude dialkyl polysulfide (B) by reacting the olefin compound (b) with sulfur in the presence of hydrogen sulfide and in the presence of a solvent, the reaction can proceed in a suitable solvent system in step 2 after the crude dialkyl polysulfide (B) is recovered by various methods such as distillation or washing with water.

The temperature of the reaction system in step 2 is preferably 40° C. to 120° C., and more preferably 50° C. to 100° C. since it is possible to effectively increase the content of dialkyl disulfide and dialkyl trisulfide and to suppress side reactions such as decomposition. In addition, the time for the reaction is usually 1 to 36 hours, and more preferably 5 to 24 hours.

In step 2, mercaptans which are produced as a by-product in step 1 are extracted with the alcohol layer using an alcohol as a solvent and including an alkali metal hydroxide in the reaction system, and as a result, a dialkyl polysulfide with less odor can be obtained among the dialkyl polysulfides (II). Examples of the alkali metal hydroxides include sodium hydroxide, potassium hydroxide, lithium hydroxide, rubidium hydroxide, cesium hydroxide, and the like. Among these, sodium hydroxide and potassium hydroxide are preferable since they have a high solubility in alcohol-based solvents.

The amount of the alkali metal hydroxide to be used is preferably 0.5 to 20 parts by mass with respect to 100 parts by mass of a crude dialkyl polysulfide (B), and more preferably 1 to 10 parts by mass since the solubility in the alcohol is maintained.

After the completion of step 2, it is also possible to obtain the dialkyl polysulfide (II) by using conventional methods for separating the liquid and filtering the solids or distilling and separating volatile content. Here, in General Formula (2), the content ratios of compounds in which there are various different n's are determined according to the peak area of a chart which is obtained by measurement known as high performance liquid chromatography (hereinafter abbreviated as "HPLC"). Here, the measurement conditions of HPLC are as described above.

The lubricating fluid composition of the present invention contains the extreme-pressure additive of the present invention and base oil. The base oil is not limited and it is possible to appropriately select and use a base oil from mineral oils and synthetic oils and the like according to the purpose and conditions of use. Examples of the mineral oils include paraffin base crude oil, intermediate base crude oil, distillate oil obtained by atmospheric distillation of naphthenic base crude oil or reduced pressure distillation of the residue after atmospheric distillation thereof, or refined oils thereof which are obtained by solvent refining, hydrogenation refining, dewaxing treatment, white clay treatment, and the like. Examples of the synthetic oils include low molecular weight polybutene, low molecular weight polypropylene, α-olefin oligomers with 8 to 14 carbon atoms and hydrides thereof, polyol esters such as fatty acid esters of trimethylolpropane or fatty acid esters of pentaerythritol, ester-based compounds such as dibasic acid esters, aromatic polycarboxylic acid esters, and phosphoric acid esters, alkyl aromatic-based compounds such as alkylbenzene and alkylnaphthalene, polyglycol oils such as polyalkylene glycol, silicone oils, and the like, and it is possible to use synthetic oils individually or to appropriately use two more types thereof together.

The mixing ratio of the extreme-pressure additive and the base oil in the lubricating fluid composition of the present invention is not particularly limited; however, the content of the extreme-pressure additive is normally 0.01 to 50 parts by mass, preferably 0.05 to 20 parts by mass, in terms of dialkyl polysulfide conversion in the extreme-pressure additive, with respect to 100 parts by mass of the base oil.

It is also possible to use the lubricating fluid composition of the present invention as a grease by further incorporating a thickener therein. Examples of the thickener which is used here include soap-based thickeners such as a metal soap type thickener or a composite soap-based thickener, or urea-based thickeners, and the like. In the case of using such a thickener, it is preferable to mix the thickner in the base oil in advance to make a uniform mixture.

The lubricating fluid composition is not limited as long as the extreme-pressure additive and the base oil are used and, for example, as additives, it is possible to appropriately use additives such as oily agents, anti-wear agents, extreme-pressure agents, other anti-rust agents, corrosion inhibitors, anti-foaming agents, cleaning dispersing agents, pour point depressants, viscosity index improvers, anti-oxidants, emulsifiers, demulsifiers, mold inhibitors, friction modifiers, and surfactants together depending on the intended use and the performance.

Specific examples of various additives include the following. As oily agents, long chain fatty acids (oleic acid) and the like; as anti-wear agents, phosphoric acid esters, metal dithiophosphate salt, and the like; as extreme-pressure agents, organic sulfur compounds, organic halogen compounds and the like; as other anti-rust agents, carboxylic acids, amines, alcohols, esters, and the like; as corrosion inhibitors, nitrogen compounds (such as benzotriazole), compounds including sulfur and nitrogen (such as 1,3,4-thiadiazolyl-2,5-bis dialkyl dithiocarbamate); as anti-foaming agents, silicone oils, metal soaps, fatty acid esters, phosphoric acid esters, and the like; as cleaning dispersing agents, neutral and basic sulfonates and phenates (metal salt form), succinimides, esters, and benzyl amine copolymer-based polymers; as pour point depressants, condensates of chlorinated paraffin with naphthalene or phenols, polyalkyl acrylates and methacrylates, polybutenes, polyalkyl styrenes, polyvinyl acetate and the like; as viscosity index improvers, polymethacrylate, polyisobutylene, olefin copolymers, polyalkyl styrene, and the like; as anti-oxidants, amines, hindered phenol, zinc thiophosphate, trialkyl phenols, and the like; as emulsifiers, sulfuric acids, sulfonic acids, and phosphoric acid esters, fatty acid derivatives, amine derivatives, quaternary ammonium salts, and polyoxyethylene-based surfactants; as demulsifiers, quaternary ammonium salts, sulfated oils, and phosphoric acid esters; as mold inhibitors, phenolic compounds, formaldehyde donor compounds, salicylanilide-based compounds, and the like.

The lubricating fluid composition is a composition in which the extreme-pressure additive, the base oil, and, if necessary, a viscous agent and other additives, are uniformly mixed. The mixing method is not particularly limited and, at this time, it is also possible to heat the mixture to 30° C. to 60° C. in order to achieve uniformity.

The application of the lubricating fluid composition of the present invention is not particularly limited, and the lubricating fluid composition of the present invention can be used as a lubricant composition, for example, and can be used as a lubricating oil for automobiles which is used in a driving system device such as an internal combustion engine, an automatic transmission, a shock absorber, and power steering, or in gears, or the like; as a metal processing oil which is used for metal working such as cutting, grinding, plastic working; and as a hydraulic oil which is a power transmission fluid which is used in operations for power transmission, power control, buffering, and the like in hydraulic systems such as hydraulic devices and apparatuses. In particular, it is also possible to favorably use the lubricating fluid composition of the present invention for the use which involves contact with a sealing agent since it is possible to reduce, when it is used as a gear oil, the swelling degree in gear box sealing agents (such as chloroprene rubber, nitrile rubber) which are used, to a greater extent than conventional products.

EXAMPLES

Detailed description will be given of the present invention with specific examples. Unless otherwise stated, "part" and "%" in the Examples are by mass.

Example 1 [Preparation of Dialkyl Polysulfide (Diisobutylene Sulfide)]

365 g of diisobutylene (3.26 mol), 104 g of powdered sulfur (3.26 mol), 0.1 g of potassium hydroxide, and 4 g of butyl carbitol were charged into a 1 liter autoclave equipped with a heating apparatus, a hydrogen sulfide blowing tube, and a hydrogen sulfide absorption apparatus. After sealing the autoclave, vacuum degassing was performed by reducing the pressure of the inside of the reaction chamber to −0.1 MPa or less using a vacuum pump. Subsequently, after sealing the autoclave, the internal temperature was increased to 120° C. 65 g (1.9 mol) of hydrogen sulfide gas (purity: 99.9 mol %) was blown into the autoclave at a pressure of 6 kg/cm$^2$ over 20 hours. Furthermore, the resultant was maintained at the same temperature for 10 hours. Subsequently, after cooling to 40° C., the pressure was returned to normal pressure by opening a valve connected to the hydrogen sulfide absorption apparatus, air was blown from the blowing tube, the residual hydrogen sulfide and unreacted diisobutylene were distilled, and thus, 469 g (87% yield) of a crude olefin sulfide (A-1) was obtained.

72 g of ethylene glycol, 73 g of sodium sulfide, and 4 g of sodium hydroxide were added to 430 g of the obtained crude sulfide olefin (A-1), after performing a reaction for 10 hours at 80° C., the ethylene glycol layer in the lower layer was separated and removed, and a pale yellow dialkyl polysulfide (1) was obtained in the upper layer. In the pale yellow dialkyl polysulfide (1), the total sulfur content ratio was 29% and the active sulfur content ratio which was measured according to ASTM-D1622, except that the processing temperature was 120° C., was 2.7%. The trisulfide content ratio in the dialkyl polysulfide was 99%, the content ratio of the tetrasulfide was 1%, and the content ratio of the monosulfide was 0%. Here, thermal decomposition temperature (50%) of dialkyl polysulfide (1) was 232° C. Here, the thermal decomposition temperature was measured by the following method.

<Measuring Method of Thermal Decomposition Temperature>

Measuring apparatus: thermogravimetric analyzer manufactured by Rigaku Corporation Temperature rising rate: 20° C./min

Example 2 [Preparation of Dialkyl Polysulfide (Sulfide Diisobutylene)]

365 g of diisobutylene (40.8 mol), 130 g of powdered sulfur (4.08 mol), 0.1 g of potassium hydroxide, and 4 g of butyl carbitol were charged into a 1 liter autoclave equipped with a heating apparatus, a hydrogen sulfide blowing tube, and a hydrogen sulfide absorption apparatus. After sealing the autoclave, vacuum degassing was performed by reducing the pressure of the inside of the reaction chamber to −0.1 MPa or less using a vacuum pump. Subsequently, after sealing the autoclave, the internal temperature was increased to 120° C. Here, 65 g (1.9 mol) of hydrogen sulfide gas (purity: 99.9 mol %) was blown into the autoclave at a pressure of 6 kg/cm$^2$ over 20 hours. In addition, the resultant was maintained at the same temperature for 10 hours. Subsequently, after cooling to 40° C., the pressure was returned to normal pressure by opening a valve connected to the hydrogen sulfide absorption apparatus, air was blown from the blowing tube, the residual hydrogen sulfide and unreacted diisobutylene were distilled, and thus, 527 g (93% yield) of a crude sulfide olefin (A-2) was obtained.

72 g of ethylene glycol, 95 g of sodium sulfide, and 4 g of sodium hydroxide were added to 430 g of the obtained crude sulfide olefin (A-2), after performing a reaction for 10 hours at 80° C., the ethylene glycol layer of the lower layer was separated and removed, and the pale yellow dialkyl polysulfide (2) was obtained in the upper layer. In the pale yellow dialkyl polysulfide (2), the total sulfur content ratio was 29% and the active sulfur content ratio which was measured according to ASTM-D1622, except that the processing temperature was 120° C., was 3.0%. The trisulfide content ratio in the dialkyl polysulfide (2) was 99%, the tetrasulfide content ratio was 1%, and the monosulfide content ratio was 0%. The thermal decomposition temperature (50%) of the dialkyl polysulfide (2) was 233° C.

Comparative Example 1 [Preparation of Comparative Dialkyl Polysulfide (Comparative Sulfide Diisobutylene)]

365 g of diisobutylene (3.26 mol), 104 g of powdered sulfur (3.26 mol), 0.1 g of potassium hydroxide, and 4 g of butyl carbitol were charged into a 1 liter autoclave equipped with a heating apparatus, a hydrogen sulfide blowing tube, and a hydrogen sulfide absorption apparatus. After sealing the autoclave, vacuum degassing was performed by reducing the pressure of the inside of the reaction chamber to −0.1 MPa or less using a vacuum pump. Subsequently, after sealing the autoclave, the internal temperature was increased to 120° C. Here, 65 g (1.9 mol) of hydrogen sulfide gas (purity: 99.9 mol %) was blown into the autoclave at a pressure of 6 kg/cm$^2$ over 20 hours. In addition, the resultant was maintained at the same temperature for 10 hours. Subsequently, after cooling to 40° C., the pressure was returned to normal pressure by opening a valve connected to the hydrogen sulfide absorption apparatus, air was blown from the blowing tube, the residual hydrogen sulfide and unreacted diisobutylene were distilled, and thus, 469 g (87% yield) of a comparative dialkyl polysulfide (1') was obtained. In the comparative dialkyl polysulfide (1'), the total sulfur content ratio was 35% and the active sulfur content ratio which was measured according to ASTM-D1622, except that the processing temperature was 120° C., was 10%. The trisulfide content ratio of the comparative dialkyl polysulfide (1') was 45%, the tetrasulfide content ratio was 45%, the pentasulfide content ratio was 10%, and the monosulfide content ratio was 0%. The thermal decomposition temperature (50%) of the comparative dialkyl polysulfide (1') was 226° C.

Comparative Example 2 (Same as Above)

365 g of diisobutylene (3.26 mol), 104 g of powdered sulfur (3.26 mol), 0.1 g of potassium hydroxide, and 4 g of butyl carbitol were charged into a 1 liter autoclave equipped with a heating apparatus, a hydrogen sulfide blowing tube, and a hydrogen sulfide absorption apparatus. After sealing the autoclave, vacuum degassing was performed by reducing the pressure of the inside of the reaction chamber to −0.1 MPa or less using a vacuum pump. Subsequently, after sealing the autoclave, the internal temperature was increased to 120° C. Here, 65 g (1.9 mol) of hydrogen sulfide gas (purity: 99.9 mol %) was blown into the autoclave at a pressure of 6 kg/cm$^2$ over 20 hours. Furthermore, the resultant was maintained at the same temperature for 10 hours. Subsequently, after cooling to 40° C., the pressure was returned to normal pressure by opening a valve connected to the hydrogen sulfide absorption apparatus, air was blown from the blowing tube, the residual hydrogen sulfide and unreacted diisobutylene were distilled, and thus, 469 g (87% yield) of a crude sulfide olefin (A-3) was obtained.

72 g of water, 73 g of sodium sulfide, and 4 g of sodium hydroxide were added to 430 g of the obtained crude sulfide olefin (A-3), after performing a reaction for 10 hours at 80° C., the water layer of the lower layer was separated and removed, and the pale yellow comparative dialkyl polysulfide (2') was obtained in the upper layer. In the pale yellow comparative dialkyl polysulfide (2'), the total sulfur content ratio was 34% and the active sulfur content ratio which was measured according to ASTM-D1622, except that the processing temperature was 120° C., was 9.5%. The trisulfide content ratio in the comparative dialkyl polysulfide (2') was 55%, the tetrasulfide content ratio was 40%, the pentasulfide content ratio was 5%, and the monosulfide content ratio was 0%. The thermal decomposition temperature (50%) of the comparative dialkyl polysulfide (2') was 246° C.

The total sulfur content ratio, the active sulfur content ratio, and the content ratios of the monosulfide, the trisulfide, the tetrasulfide, and the pentasulfide of the dialkyl polysulfides (1) to (2) and the comparative dialkyl polysulfides (1') to (2') are respectively shown in Table 1. [Table 1]

TABLE 1

|  | Example | | Comparative Example | |
| --- | --- | --- | --- | --- |
|  | 1 | 2 | 1 | 2 |
| Dialkyl polysulfide | (1) | (2) | (1') | (2') |
| Total sulfur content ratio (%) | 29 | 29 | 35 | 34 |
| Active sulfur content ratio (%) | 2.7 | 3.0 | 10.0 | 9.5 |
| Dialkyl monosulfide content ratio (%) | 0 | 0 | 0 | 0 |
| Dialkyl disulfide content ratio (%) | 0 | 0 | 0 | 0 |
| Dialkyl trisulfide content ratio (%) | 99 | 99 | 45 | 55 |
| Dialkyl tetrasulfide content ratio (%) | 1 | 1 | 45 | 40 |
| Dialkyl pentasulfide content ratio (%) | 0 | 0 | 10 | 5 |
| Thermal decomposition temperature (50%, ° C.) | 234 | 233 | 226 | 228 |

Example 3 (Lubricating Fluid Composition)

A lubricating fluid composition (1) of the present invention was obtained by mixing dialkyl polysulfide (1) into mineral oil with a viscosity at 40° C. of 11 mm$^2$/s such that its content ratio is adjusted to be 5 mass % based on the total mass of all the dialkyl polysulfide in the dialkyl polysulfide (1). Using the lubricating fluid (1), the corrosion of the metal surface and the formability of a coating film of metal sulfide on the metal surface were evaluated according to the methods described below. The evaluation results are shown in Table 2.

<Method for Evaluating Corrosion of Metal Surface>

The corrosion state of a copper plate surface was confirmed by performing a copper plate corrosion test using the method according to JIS K2513. The test conditions were set to 100° C. and 3 hours.

<Method for Evaluating Formability of Coating Film of Metal Sulfide on Metal Surface>

The weld load was measured using a shell-type four-ball tester according to the method set out in ASTM D-2783.

Example 4 (Same as Above)

A lubricating fluid composition (2) was obtained in the same manner as in Example 3 except that the dialkyl polysulfide (2) was used instead of the dialkyl polysulfide (1). Evaluation was carried out in the same manner as in Example 3 and the results are shown in Table 2.

Example 5 (Same as Above)

<Preparation of Dialkyl Polysulfide (II)>

320 g of 1-decene, 73 g of powdered sulfur, 0.1 g of potassium hydroxide, and 4 g of butyl carbitol were charged into a 1 liter autoclave equipped with a heating apparatus, a hydrogen sulfide blowing tube, and a hydrogen sulfide absorption apparatus. After sealing the autoclave, vacuum degassing was performed by reducing the pressure of the inside of the reaction chamber to −0.1 MPa or less using a vacuum pump. Subsequently, the internal temperature was increased to 120° C. Here, 43 g of hydrogen sulfide gas (purity: 99.9 mol %) was blown into the autoclave at a pressure of 6 kg/cm$^2$ over 20 hours. Furthermore, after raising the temperature to 180° C., the temperature was maintained for 24 hours. Subsequently, after cooling to 40° C., the pressure was returned to normal pressure by opening a valve connected to the hydrogen sulfide absorption apparatus, air was blown from the blowing tube, the residual hydrogen sulfide was distilled, and a crude sulfide olefin was obtained. 72 g of ethylene glycol, 73 g of sodium sulfide, and 4 g of sodium hydroxide were added to 430 g of a crude sulfide olefin, and a reaction was carried out at 60° C. for 10 hours. After the reaction, the ethylene glycol layer of the lower layer was separated and removed, and thus, pale yellow dialkyl polysulfide (II-1) in the upper layer was obtained. In the dialkyl polysulfide (II-1), the total sulfur content ratio was 23%, the active sulfur content ratio was 5%, the total content ratio of dialkyl polysulfide in which n in General Formula (2) is 2 and dialkyl polysulfide in which n in General Formula (2) is 3 was 87%, and the thermal decomposition temperature of the dialkyl polysulfide (II-1) was 272° C.

<Preparation of Lubricating Fluid Composition (3)>

A lubricating fluid composition (3) was obtained in the same manner as in Example 3 except for using a combination of the dialkyl polysulfide (1) and dialkyl polysulfide (II-1) at a mass ratio of 3:1. Evaluation was carried out in the same manner as in Example 3 and the results are shown in Table 2.

Comparative Example 3 (Comparative Lubricating Fluid Composition)

A comparative lubricating fluid composition (1') was obtained in the same manner as in Example 3 except that the comparative dialkyl polysulfide (1') was used instead of dialkyl polysulfide (1). Evaluation was carried out in the same manner as in Example 3 and the results are shown in Table 2.

Comparative Example 4 (Same as Above)

A comparative lubricating fluid composition (2') was obtained in the same manner as in Example 3 except that the comparative dialkyl polysulfide (2') was used instead of the dialkyl polysulfide (1). Evaluation was carried out in the same manner as in Example 3 and the results are shown in Table 2. [Table 2]

TABLE 2

|  | Example | | | Comparative Example | |
| --- | --- | --- | --- | --- | --- |
|  | 3 | 4 | 5 | 3 | 4 |
| Lubricating fluid composition | (1) | (2) | (3) | (1') | (2') |
| Dialkyl polysulfide used | (1) | (2) | (1) + (II-1) | (4) | (5) |
| Content ratio of dialkyl polysulfide in mineral oil (mass %) | 5 | 5 | 5 | 5 | 5 |
| Corrosion of metal surface | 2a | 2a | 1b | 4c | 4c |
| Formability of coating film of metal sulfide [N(kgf)] | 2744 (280) | 2744 (280) | 2207 (225) | 2744 (280) | 2744 (280) |

The invention claimed is:

1. A method for producing dialkyl polysulfide, comprising:
   a first step of reacting an olefin compound (a) represented by General Formula (1): $R^1R^2C=CHR^3$ (where $R^1$ and $R^2$ each are an alkyl group, $R^3$ is a hydrogen atom or an alkyl group, and the total number of carbon atoms of $R^1$, $R^2$ and $R^3$ is 2 to 20) with sulfur in the presence of a hydrogen sulfide to thereby obtain a crude dialkyl polysulfide (A), and
   a second step of reacting the crude dialkyl polysulfide (A) and a sulfide of an alkali metal in a solvent including an alcohol to reduce the number of sulfur atoms in the crude dialkyl polysulfide (A)
   wherein, in the first step, the reaction is performed at 120° C. to 150° C. for 1 to 72 hours, and in the second step, the reaction is performed at 40° C. to 80° C. for 1 to 72 hours, and
   wherein, in the second step, the content of the alcohol in the solvent including the alcohol is 45 to 75 parts by mass with respect to 100 parts by mass of the solvent; the amount of the solvent is 50 mass % to 300 mass % with respect to the mass of the sulfide of the alkali metal.

2. The method for producing dialkyl polysulfide according to claim 1,
   wherein, in General Formula (1), the total number of carbon atoms of $R^1$ and $R^2$ is 2 to 14 and $R^3$ is a hydrogen atom.

3. The method for producing dialkyl polysulfide according to claim 1,
   wherein the olefin compound (a) is diisobutylene.

4. The method for producing dialkyl polysulfide according to claim 1,
   wherein the alcohol is ethylene glycol.

5. The method for producing dialkyl polysulfide according to claim 1,
   wherein the first step is performed in the presence of a basic compound.

6. The method for producing dialkyl polysulfide according to claim 5,
   wherein the basic compound is sodium hydroxide or potassium hydroxide.

7. The method for producing dialkyl polysulfide according to claim 1,
   wherein, in the first step, the reaction of the olefin compound (a) represented by General Formula (1) with sulfur is performed at 120° C. to 130° C. for 5 to 48 hours.

8. The method for producing dialkyl polysulfide according to claim 1,
   wherein the sulfide of an alkali metal is sodium sulfide.

9. The method for producing dialkyl polysulfide according to claim 1,
   wherein the second step is performed in the presence of a hydroxide of an alkali metal.

10. The method for producing dialkyl polysulfide according to claim 9,
    wherein the hydroxide of an alkali metal is sodium hydroxide or potassium hydroxide.

11. The method for producing dialkyl polysulfide according to claim 1,
    wherein the dialkyl polysulfide is represented by General formula (2):

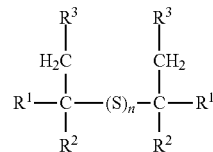

(2)

wherein $R^1$ and $R^2$ each are an alkyl group, $R^3$ is a hydrogen atom or an alkyl group, the total number of carbon atoms of one of $R^1$, one of $R^2$, and one of $R^3$ is 2 to 20, and n is an integer of 1 to 6,
the sum of the content ratio of the compound of General Formula (2) in which n is 2 and the content ratio of the compound of General Formula (2) in which n is 3 being 80 mass % to 100 mass % with respect to the total amount of the compound represented by General Formula (2).

12. An extreme-pressure additive comprising:
    a dialkyl polysulfide (I) obtained by the method for producing dialkyl polysulfide according to claim 1 and further comprising
    a dialkyl polysulfide other than the dialkyl polysulfide (I); and
    wherein the dialkyl polysulfide other than the dialkyl polysulfide (I) is a dialkyl polysulfide (II) represented by General Formula (3):

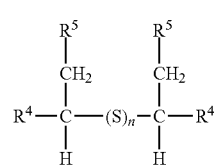

(3)

wherein $R^4$ and $R^5$ each are a hydrogen atom or an alkyl group, the total number of carbon atoms of one of $R^4$ and one of $R^5$ is 4 to 20, and n is an integer of 1 to 6, the sum of the content ratio of the compound of General Formula (3) in which n is 2 and the content ratio of the compound of General Formula (3) in which n is 3 being 80 mass % to 100 mass % with respect to the total amount of the compound represented by General Formula (3).

13. The extreme-pressure additive according to claim 12, wherein the dialkyl polysulfide (I) is represented by General formula (2):

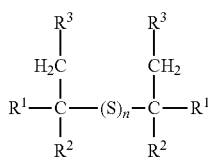

(2)

wherein $R^1$ and $R^2$ each are an alkyl group, $R^3$ is a hydrogen atom or an alkyl group, the total number of carbon atoms of one of $R^1$, one of $R^2$, and one of $R^3$ is 2 to 20, and n is an integer of 1 to 6, the sum of the content ratio of the compound of General Formula (2) in which n is 2 and the content ratio of the compound of General Formula (2) in which n is 3 being 80 mass % to 100 mass % with respect to the total amount of the compound represented by General Formula (2).

14. A lubricating fluid composition comprising:
the extreme-pressure additive according to claim 12; and
a base oil.

15. A lubricating fluid composition comprising:
the extreme-pressure additive according to claim 13; and
a base oil.

16. The method for producing dialkyl polysulfide according to claim 3,
Wherein the amount of active sulfur in the dialkyl polysulfide is 0.1 mass % to 30 mass % based on the total sulfur content.

* * * * *